United States Patent [19]

Bell et al.

[11] Patent Number: 4,927,924
[45] Date of Patent: May 22, 1990

[54] SYNTHESIS OF CAPROLACTAM

[75] Inventors: Weldon K. Bell, Pennington; Werner O. Haag, Lawrenceville, both of N.J.

[73] Assignee: Mobil Oil Corp., New York, N.Y.

[21] Appl. No.: 338,015

[22] Filed: Apr. 14, 1989

[51] Int. Cl.$^5$ ............................................. C07D 201/04
[52] U.S. Cl. ....................................... 540/536; 540/535
[58] Field of Search .................................. 540/535, 536

[56] References Cited

U.S. PATENT DOCUMENTS 3,503,958  3/1970  Landis ................................. 540/535
4,359,421 11/1982  Bell et al. ........................... 340/535
4,697,010  9/1987  McMahon ........................... 540/536
4,709,024 11/1987  Sato et al. .......................... 540/535

Primary Examiner—Robert T. Bond
Attorney, Agent, or Firm—Alexander J. McKillop; Charles J. Speciale; Dennis P. Santini

[57] ABSTRACT

A process is provided for catalytically converting cyclohexanone oxime to epsilon caprolactam. The conversion is characterized by exceptionally high selectivity and reduced rate of catalyst aging, even at single pass conversion above 90 percent. The conversion catalyst is a medium pore size crystalline zeolite exemplified by ZSM-5 which has low acid activity. Recycling unconverted oxime provides excellent ultimate yield of caprolactam.

16 Claims, 2 Drawing Sheets

SYNTHESIS OF CAPROLACTAM

FIELD OF THE INVENTION

This invention relates to an improved process for the catalyzed conversion of oximes to amides. More particularly, it relates to a highly selective gas phase catalyzed conversion of cyclohexanone oxime to epsilon caprolactam over a crystalline zeolite catalyst composition of controlled acidity.

BACKGROUND OF THE INVENTION

Epsilon caprolactam, usually referred to simply as "caprolactam", is a large volume commodity chemical used as a monomer in the production of the commercially important Nylon-6. Although routes to the precursor cyclohexanone oxime vary, all commercial caprolactam production makes use of a Beckmann rearrangement of the oxime. The commercial reaction is carried out in a batch operation in oleum ($H_2SO_4 \cdot SO_3$) solution. The recovery step in this technology employs an ammonium hydroxide neutralization of the resulting caprolactam-oleum solution, a process generating two moles of by-product ammonium sulfate per mole of product. The sulfate has some value as a low grade fertilizer, but its recovery and/or disposal can add substantial cost to Nylon-6 production. Attempts have been made to circumvent the use of oleum and carry out the reaction in the gas phase, thereby eliminating the undesirable by-product.

A number of patents and publications have appeared which describe such heterogeneous gas phase conversions. Examples of these include U.S. Pat. No. 3,503,958 to P. S. Landis, which describes and claims such conversion using a zeolite such as hydrogen Y; U.S Pat. No. 3,016,375 which uses as catalyst polyphosphoric acid; and U.S. Pat. No. 4,359,421 to Bell et al. which uses as catalyst a zeolite having a silica to alumina ratio of at least 12 and a Constraint Index of 1 to 12. The foregoing patents are incorporated herein by reference for background purposes.

U.S. Pat. No. 4,582,815 to Bowes describes and claims a method for preparing binder-free and silica-bonded extrudates of zeolites, including ZSM-5. The entire contents thereof are incorporated herein by reference as if fully set forth.

The desired rearrangement of cyclohexanone oxime (I) to caprolactam (II) is believed to occur via a protonated intermediate (not shown), according to Equation A.

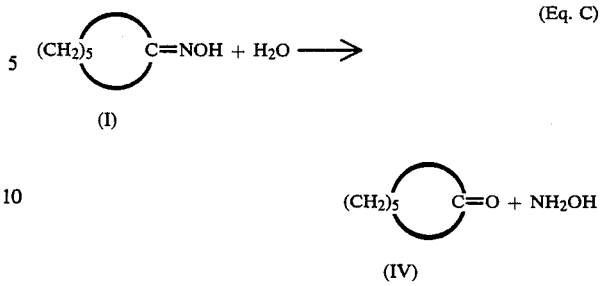

In addition, however, two major side reactions occur, one with the formation of 5-cyanopentene (III) and water (Equation B), and the other forming cyclohexanone (IV) (Equation C).

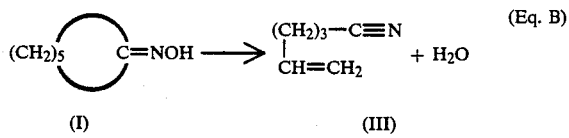

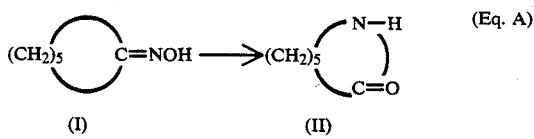

In addition to (III) and (IV) other by-products of unknown structure also are formed.

While the heterogeneous gas phase processes described above for conversion of cyclohexanone oxime to caprolactam all avoid the problems associated with the ammonium bisulfate product formed in the conventional oleum process, these processes in general tend to form an uneconomically large amount of organic by-products. There is evident need for a heterogeneous process which is highly selective for the desired epsilon caprolactam product.

We have now found that an unexpected, large increase in selectivity is obtained when cyclohexanone oxime is converted to epsilon caprolactam using, as catalyst, an intermediate pore-size zeolite having acid activity within a prescribed range. The improved selectivity is accompanied by better (slower) aging of the catalyst.

SUMMARY OF THE INVENTION

Figure 1A:
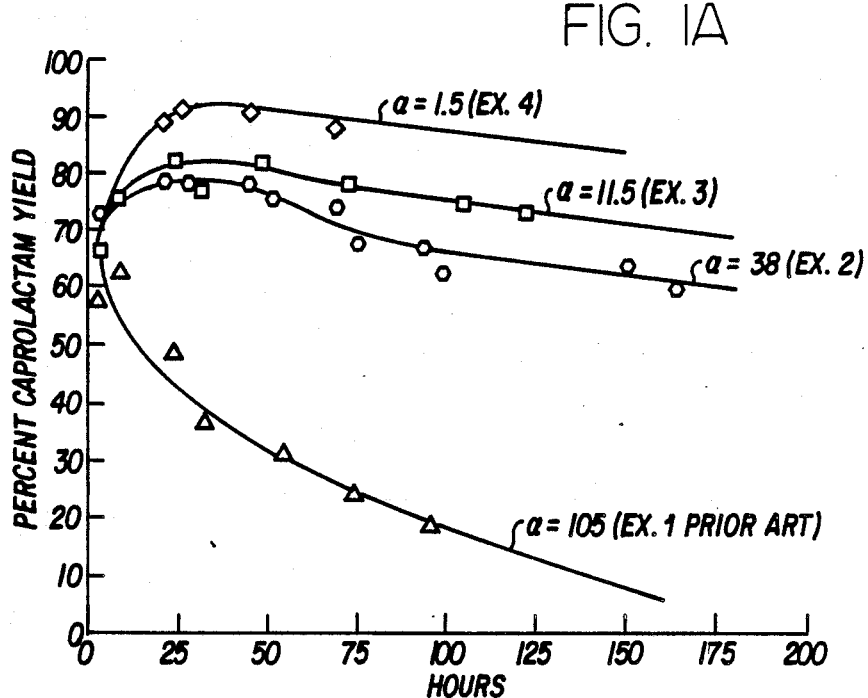
FIGS. 1A and 1B Yield and Selectivity of Steamed and Unsteamed Catalysts.

In one embodiment, this invention provides a catalytic process for manufacturing epsilon-caprolactam, said process comprising:

contacting cyclohexanone oxime under conversion conditions with a catalyst comprising a crystalline zeolite having a silica to alumina ratio of at least 12 and a Constraint Index of 1 to 12, selected from the group consisting of ZSM-5, ZSM-11, ZSM-12, ZSM-23 and ZSM-48, said crystalline zeolite having an Alpha Value of about 0.1 to about 50; and, recovering epsilon-caprolactam, all as more fully described hereinbelow.

PREFERRED EMBODIMENTS AND BEST MODE

The conversion reaction of this invention is desirably carried out in a conventional fixed bed reactor, although an ebullated or fluidized bed or other type of reactor can be useful, too, with appropriate changes in the particle size and other physical attributes of the catalyst, such as attrition resistance. The reaction temperature is in the range of about 150° to about 500° C., and more preferably between about 200° and about 400° C. Although the reaction can be carried out at atmospheric pressure, elevated pressure from about 10 psig to about 400 psig, more preferably from about 50 psig to about 300 psig, is desirable.

It is contemplated that the cyclohexanone feed to the process of this invention may be passed to the reactor neat, i.e. as undiluted solid, melt or vapor, or it may be diluted with an essentially inert solvent. The use of inert solvent provides a convenient means for storing and transferring the cyclohexanone oxime to the reaction zone. The term "inert solvent" as used herein means a solvent which does not react with the oxime or its reaction product under conversion conditions, and which is not itself converted to a significant extent when contacted with the catalyst under conversion conditions. Useful solvents include the lower boiling saturated hydrocarbons such as hexane, and aromatic compounds such as benzene. Regardless whether the cyclohexanone feed is undiluted or dissolved in inert solvent, a carrier gas may be used with the feed to help displace reaction product and any unconverted oxime from the catalyst. Among the gases which may be used are hydrogen, nitrogen, helium, carbon monoxide, carbon dioxide, sulfur dioxide and the like. Regardless of how the cyclohexanone oxime is introduced, it is contemplated that useful conversion will be obtained at a LHSV (i.e. volumes of cyclohexanone oxime feed per volume of catalyst) within the range of about 0.002 to about 5.0.

The members of the class of zeolites contemplated as useful herein have an effective pore size of generally from about 5 to about 8 angstroms, such as to freely sorb normal hexane. Such zeolites are sometimes referred to as "intermediate pore size zeolites". These structures provide constrained access to (and egress from) the internal pore structure for large molecules. Such constrained access may be material in achieving high selectivity.

A convenient measure of the extent to which a zeolite provides controlled access to molecules of varying sizes is the Constraint Index (CI) of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually have pores of large size, e.g. greater than 8 angstroms. The method by which Constraint Index is determined is described fully in U.S. Pat. No. 4,016,218, incorporated herein by reference for details of the method.

Constraint Index (CI) values for some typical materials (some of which are outside the scope of the present invention)

|  | CI | (at test temperature) |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such values are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, or the presence of possibly occluded contaminants and binders intimately combined with the zeolite, may affect the CI. It will accordingly be understood to those skilled in the art that the CI, as utilized herein, while affording a highly useful means for characterizing the zeolites of interest, is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of highly siliceous zeolites defined herein is exemplified by ZSM-5, ZSM-11, ZSM-12, ZSM-23, ZSM-35, ZSM-38, ZSM 48, and other similar materials.

U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intra-crystalline free space is occupied by organic species from the forming solution. These organic templates are removed by heating in an inert atmosphere at 1000° F. for one hour, for example, followed by base exchange with ammonium salts followed by calcination at 1000° F. in air.

The ZSM-5 type zeolites referred to herein have a crystal framework density in the dry hydrogen form, of not less than about 1.6 grams per cubic centimeter. The dry density for known crystal structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, Apr. 1967," published by the Society of Chemical Industry, London, 1968. When the crystal structure is unknown, the crystal framework density may be determined by classical pycnometer techniques. For example, it may be determined by immersing the dry hydrogen form of the zeolite in an organic solvent not sorbed by the crystal. Or, the crystal density may be determined by mercury porosimetry, since mercury will fill the interstices between crystal but not the zeolitic pores themselves.

For purposes of the present invention, ZSM-5, ZSM-11, ZSM12, ZSM-23 and ZSM-48 are preferred, with ZSM-5 and ZSM-11 particularly preferred.

It is important for purposes of the present invention to control the acid activity of the catalyst such that its Alpha Value be within the broad range of 0.1 to about 50, and preferably about 0.5 to about 40, and most preferably about 1.0 to about 15.

The Alpha Value referred to herein is an experimentally determined number that gives an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant= 0.016 sec$^{-1}$). The Alpha Test is described in U.S. Pat. No. 3,354,078, in the *Journal of Catalysis*, Vol. 4, p. 527 (1965): Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

A preferred way for controlling the acid activity of the zeolite is by treatment with steam at high temperature, as illustrated hereinbelow by example. Control of silica to alumina ratio during synthesis of the zeolite is another preferred means. Other known means for obtaining an Alpha Value of 0.1 to 50 are less preferred.

Whereas the crystalline zeolite described above preferably is self-bonded, it also may be incorporated in a matrix. We have found, however, that selectivity of such matrix-bonded catalyst is well maintained only if the matrix is substantially non-acidic. Suitability of a matrix material for purposes of this invention can be readily judged by comparing the bonded material with self-bonded zeolite to see if the matrix material has a significant adverse effect on selectivity. A preferred non-acidic matrix material is silica. Preparation of self-bound (i.e. without added binder) and of silica-bound ZSM-5 are described in U.S. Pat. No. 4,582,815 to Bowes, incorporated herein by reference for said description. Such preparation, per se, is not considered part of the present invention.

Catalyst that have become deactivated during use are readily restored to full activity by periodic regeneration at high temperature, such as 550° to about 700° C., in the presence of oxygen gas. In some instances desorption of adsorbed or occluded matter at about 500° C. in flowing nitrogen gas or hydrogen gas may effect sufficient restoration of activity.

EXAMPLES

In Examples 1–4, four catalysts are evaluated for selectivity and aging rate. The catalysts were all prepared by self-bonding 100% ZSM-5 crystals to form 1/16th inch extrudate with a length to diameter ratio of about 2, as described hereinabove, and further treated as described in the specific examples. The ZSM-5 crystals had a silica to alumina ratio of 70:1.

In all of the Examples herein described, the catalysts were tested in a down flow ⅜ inch OD tubular reactor where bed length/diameter varied from about 8 to 12. A 5 wt% solution of cyclohexanone oxime in benzene, dried with 4A molecular sieve, was charged to the reactor along with a carrier of nitrogen gas with the reaction zone (in the middle of a three zone furnace) at 300° C. and the reactor exit at atmospheric pressure. Products were condensed in a cold trap (3° C.) and analyzed by capillary gas chromatography. Caprolactam and the two main by-products, cyclohexanone oxime and cyanopentene, were identified. However, several additional minor by-products were not identified, for example, materials appearing in the GC before the oxime are summed as "light unknowns", while those appearing after caprolactam are grouped as "heavy unknowns".

For the data reported here, the standard test reaction conditions were at a 5 wt% cyclohexanone oxime in benzene fed at the rate of 1 LHSV (of solution) and a nitrogen feed of about 645 GHSV; 300° C., and 1 atm. After about 2 hours and once daily the reactor was operated for about a 2-hour period at feeds of 3 and 9 times these rates to investigate the selectivity of the catalyst at lower conversions.

EXAMPLE 1

(Prior Art)

In this Example no treatment was used. The catalyst had an Alpha Value of 105. The results are summarized in Table I.

TABLE I

| Example 1 (Prior Art) | | | | | | | |
|---|---|---|---|---|---|---|---|
| Hours on Stream | 2 | 8 | 23 | 32 | 54 | 74 | 96 |
| LHSV* | 1.1 | 1.1 | 1.1 | 1.1 | 1.1 | 1.1 | 1.1 |
| GHSV* | 991 | 993 | 992 | 987 | 987 | 990 | 997 |
| Oxime Conv., wt % | 99.5 | 91.3 | 70.7 | 46.8 | 37.7 | 29.9 | 30.2 |

TABLE I-continued

| | Example 1 (Prior Art) | | | | | | |
|---|---|---|---|---|---|---|---|
| Caprolactam yld, % | 58.2 | 62.3 | 49.2 | 36.9 | 31.3 | 24.8 | 19.2 |
| Selectivity, wt % | | | | | | | |
| Caprolactam | 58.5 | 68.3 | 69.6 | 79.0 | 83.0 | 82.9 | 63.6 |
| Cyclohexanone | 16.9 | 13.8 | 12.1 | 7.0 | 5.3 | 5.3 | 22.8 |
| Cyanopentene | 2.5 | 0.7 | 0.8 | 0.9 | 1.2 | 0.7 | 3.3 |
| Light Unknown | 8.8 | 8.9 | 6.8 | 5.2 | 3.7 | 2.9 | 6.8 |
| Heavy Unknown | 13.2 | 8.4 | 10.7 | 7.9 | 6.7 | 8.2 | 3.5 |

*In Table I and the tables which follow, LHSV (liquid hourly space velocity) and GHSV (gas hourly space velocity) are as described hereinabove under "Examples".

EXAMPLE 2

In this example, a portion of the same self-bound catalyst as used in Example 1 was treated in 100% steam at 1 atm at 900° to 1100° F. during a 5 minute period and then at 1100° F. for 30 minutes. The resulting catalyst had an Alpha Value of 38.

The catalyst was evaluated for oxime conversion and selectivity as in Example 1. In addition, after 164 hours on stream, when conversion had dropped to 63.6%, the LHSV was reduced from 1.0 to 0.5. As can be seen, this restored both conversion and selectivity to over 90%. The results are summarized in Table II.

Figure 1B:
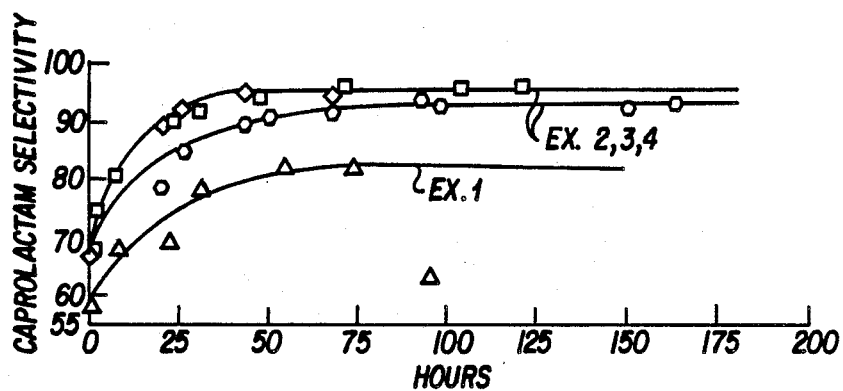

It is evident from Table II and FIGS. 1 that a remarkable increase in selectivity with a simultaneous reduction in aging results from reducing the acid activity of the catalyst from 105 (Example 1) to 38 (Example 2).

TABLE II

| | Alpha Value = 38 | | | | | | | |
|---|---|---|---|---|---|---|---|---|
| Hours On Stream | 2 | 20 | 26 | 43 | 50 | 68 | 74 | 93 |
| LHSV | 1.0 | 1.0 | 1.0 | 1.0 | 1.0 | 1.0 | 1.0 | 1.0 |
| GHSV | 897 | 907 | 898 | 904 | 890 | 890 | 887 | 887 |
| Oxime Conv., wt % | 97.7 | 99.6 | 92.3 | 87.3 | 83.2 | 80.8 | 72.4 | 71.3 |
| Caprolactam yld, % | 73.2 | 78.9 | 78.8 | 78.6 | 76.1 | 74.4 | 67.4 | 67.0 |
| Selectivity, wt % | | | | | | | | |
| Caprolactam | 74.9 | 79.2 | 85.4 | 90.0 | 91.5 | 92.0 | 93.2 | 94.0 |
| Cyclohexanone | 16.2 | 13.5 | 8.8 | 5.4 | 4.4 | 3.9 | 3.2 | 2.7 |
| Cyanopentene | 3.1 | 1.6 | 0.8 | 0.4 | 0.3 | 0.3 | 0.3 | 0.3 |
| Light Unknown | 5.0 | 5.0 | 4.2 | 3.5 | 3.3 | 3.3 | 3.1 | 2.9 |
| Heavy Unknown | 0.7 | 0.5 | 0.8 | 0.6 | 0.5 | 0.5 | 0.3 | 0.2 |
| Hours On Stream | 98 | 150 | 164 | 171 | 179 | 190 | 203 | 213 |
| LHSV | 1.0 | 1.0 | 1.0 | 0.5 | 0.5 | 0.5 | 0.5 | 0.5 |
| GHSV | 875 | 890 | 890 | 396 | 118 | 118 | 118 | 118 |
| Oxime Conv., wt % | 66.9 | 68.2 | 63.6 | 89.8 | 98.0 | 95.3 | 94.4 | 91.4 |
| Caprolactam yld, % | 62.2 | 63.4 | 59.7 | 84.8 | 88.7 | 87.0 | 86.6 | 83.2 |
| Selectivity, wt % | | | | | | | | |
| Caprolactam | 93.0 | 93.0 | 93.9 | 94.4 | 90.4 | 91.3 | 91.7 | 91.1 |
| Cyclohexanone | 3.0 | 3.5 | 2.9 | 2.5 | 5.7 | 5.3 | 5.1 | 5.5 |
| Cyanopentene | 0.4 | 0.2 | 0.2 | 0.1 | 0.7 | 0.7 | 0.7 | 0.7 |
| Light Unknown | 3.4 | 3.0 | 2.8 | 2.7 | 2.9 | 2.5 | 2.2 | 2.4 |
| Heavy Unknown | 0.2 | 0.3 | 0.1 | 0.2 | 0.2 | 0.2 | 0.2 | 0.3 |

EXAMPLE 3

Alpha Value = 11.5

For this example, another portion of the same self-bonded catalyst as was used in the prior examples was treated in 100% steam at 1 atm and 1300° F. for 20 minutes. The resulting Alpha Value was 11.5. The catalyst was evaluated as in the prior examples. Representative results are shown in Table III and in FIG. 1. As can be seen, some further improvement in selectivity and catalyst aging are obtained with reduction of Alpha Value from 38 (Example 2).

TABLE III

| | Alpha Value = 11.5 | | | | | | |
|---|---|---|---|---|---|---|---|
| Hours on Stream | 2 | 7 | 23 | 30 | 47 | 71 | 121 |
| LHSV | 1.0 | 1.0 | 1.0 | 1.0 | 1.0 | 1.0 | 1.0 |
| GHSV | 904 | 897 | 895 | 907 | 891 | 895 | 895 |
| Oxime Conv., wt % | 96.9 | 93.1 | 90.9 | 84.3 | 86.1 | 81.4 | 76.1 |
| Caprolactam yld, % | 66.2 | 75.7 | 82.3 | 77.7 | 81.4 | 78.1 | 73.2 |
| Selectivity, wt % | | | | | | | |
| Caprolactam | 68.3 | 81.3 | 90.6 | 92.2 | 94.5 | 96.0 | 96.2 |
| Cyclohexanone | 21.1 | 12.7 | 5.7 | 4.2 | 2.8 | 1.8 | 1.5 |
| Cyanopentene | 3.9 | 0.9 | 0.4 | 0.5 | 0.4 | 0.2 | 0.2 |
| Light Unknown | 5.8 | 4.0 | 2.5 | 2.6 | 2.1 | 1.8 | 2.0 |
| Heavy Unknown | 0.9 | 1.1 | 0.8 | 0.5 | 0.2 | 0.2 | 0.1 |

EXAMPLE 4

Figure 2:
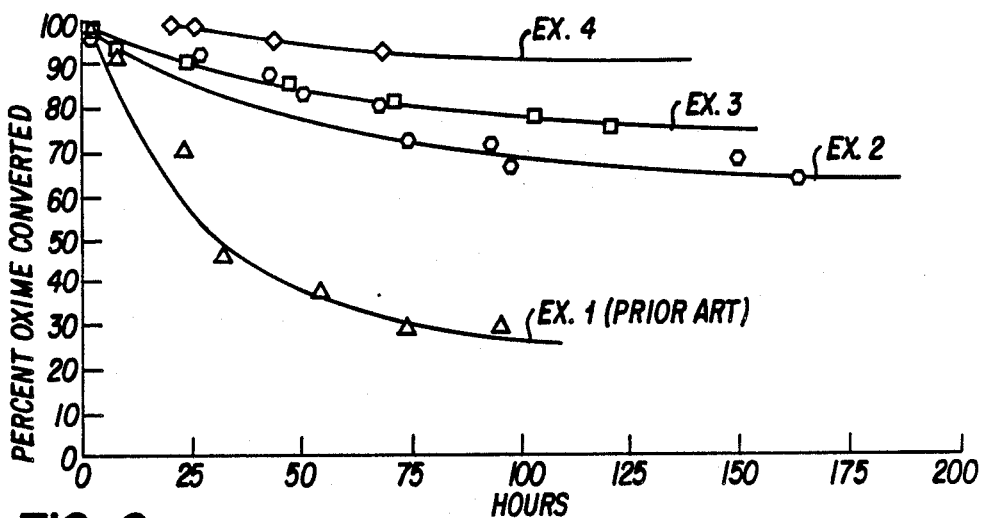
FIG. 2. Aging of Steamed and Unsteamed Catalysts.

This example illustrates that the advantages of this invention persist even for catalysts with very low acid activity. For this example, another portion of the self-bonded catalyst as was used in the prior examples was treated in 100% steam at 1 atm and 1300° F. for 7 hours. The Alpha Value which resulted was 1.5. Representative results are summarized in Table IV and in FIG. 1, which also shows the results for Examples 1-3. FIG. 2 compares aging of the prior art catalyst (Example 1) with steamed catalyst (Examples 2-4).

TABLE IV

| | Alpha Value = 1.5 | | | | | | |
|---|---|---|---|---|---|---|---|
| Hours on Stream | 1 | 3 | 20 | 21 | 25 | 44 | 68 |
| LHSV | 0.9 | 3.2 | 0.9 | 3.1 | 1.0 | 1.0 | 1.2 |
| GHSV | 916 | 2679 | 920 | 2662 | 937 | 944 | 972 |
| Oxime Conv., wt % | 96.1 | 99.7 | 99.3 | 82.3 | 99.2 | 95.6 | 93.1 |
| Caprolactam yld, % | 64.5 | 77.7 | 89.1 | 73.7 | 91.3 | 91.1 | 88.2 |
| Selectivity, wt % | | | | | | | |
| Caprolactam | 67.1 | 77.9 | 89.8 | 89.6 | 92.1 | 95.3 | 94.8 |

TABLE IV-continued

| | Alpha Value = 1.5 | | | | | | |
|---|---|---|---|---|---|---|---|
| Cyclohexanone | 14.6 | 14.2 | 6.1 | 6.6 | 4.6 | 2.3 | 2.3 |
| Cyanopentene | 2.1 | 1.3 | 0.5 | 0.7 | 0.5 | 0.4 | 0.4 |
| Light Unknown | 6.5 | 5.5 | 3.3 | 2.7 | 2.3 | 2.0 | 2.4 |
| Heavy Unknown | 9.8 | 1.1 | 0.3 | 0.5 | 0.5 | 0.1 | 0.1 |

EXAMPLE 5

This example compares the behavior of the steamed, selfbound catalyst such as was used in Example 4 with a steamed ZSM-5 zeolite in an alumina matrix. For the latter catalyst, a ZSM-5 extrudate bound with 35% Kaiser gamma alumina was used. The zeolite component is a hydrogen form of ZSM-5 of nominal 70:1 $SiO_2/Al_2O_3$ ratio, ammonium exchanged, and air calcined at 1000° F. The Alpha Value of the fresh extrudate, which was 206 before steaming, was reduced to 0.9 by treatment in 100% steam (1 atm) at 1300° F. for 7 hours.

Figure 3A:
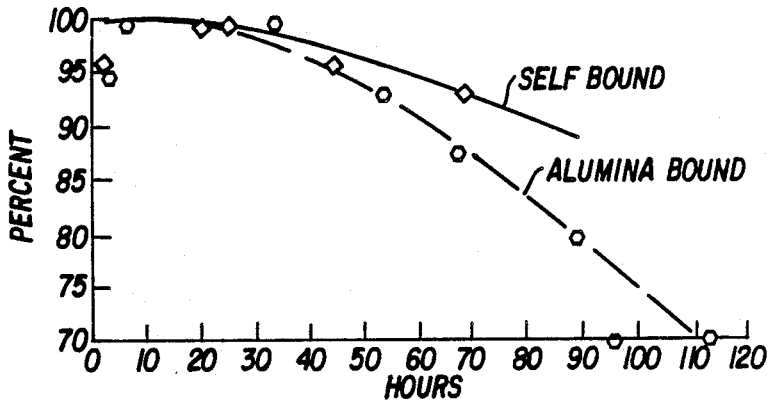
FIGS. 3A and 3B. Comparison of Alumina-Bound and Self-Bound Catalyst.
Figure 3B:
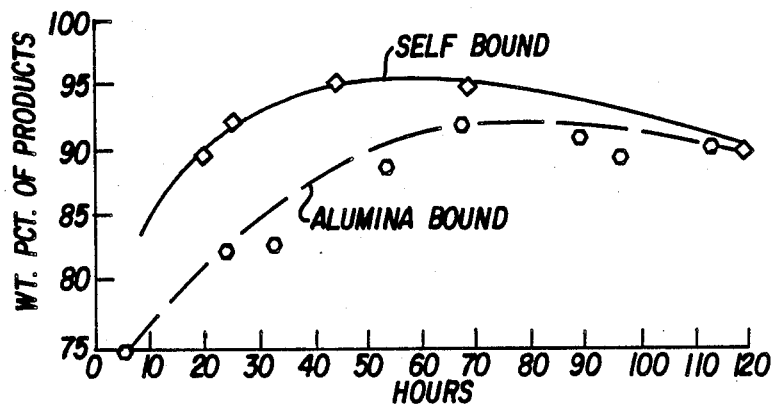

Each catalyst was evaluated by the same method and under the same conditions of temperature and LHSV a used in Examples 1–4. Representative results for conversion and selectivity of the two catalysts are compared in FIG. 3. As can be seen in FIG. 3, the self-bound catalyst provided better selectivity and aging.

What is claimed is:

1. In a process for manufacturing epsilon-caprolactam by contacting cyclohexanone under conversion conditions with bonded particles of a crystalline zeolite catalyst, said zeolite having a silica to alumina ratio of at least 12, a Constraint Index of 1 to 12, and an Alpha Value higher than 50, the improvement comprising:
   steaming said zeolite prior to said contacting step to reduce its Alpha Value to about 0.1 to 50, thereby increasing the selectivity and decreasing the aging rate of said catalyst.

2. The process described in claim 1 wherein said zeolite has an Alpha Value of at least about 100 prior to said steaming step.

3. The process described in claim 2 wherein said Alpha Value is about 0.5 to about 40.

4. The process described in claim 2 wherein said bonded particles include a substantially non-acidic matrix.

5. The process described in claim 4 wherein said matrix is silica.

6. The process described in claim 2 wherein said crystalline zeolite is self-bonded.

7. The process described in claim 3 wherein said catalyst consists essentially of said crystalline zeolite.

8. The process described in claim 2 wherein said conversion conditions include a temperature of about 200° to about 400° C.

9. The process described in claim 2 wherein said crystalline zeolite has the crystal structure of ZSM-5, ZSM-11 or ZSM-23.

10. The process described in claim 6 wherein said crystalline zeolite has the crystal structure of ZSM-5, ZSM-11 or ZSM-23.

11. A catalytic process for manufacturing epsilon-caprolactam, said process comprising:
    contacting cyclohexanone oxime under conversion conditions with a steamed catalyst comprising a crystalline aluminosilicate zeolite selected from the group consisting of ZSM-5, ZSM-11, ZSM-12, ZSM-23 and ZSM-48, said crystalline aluminosilicate zeolite having an Alpha Value of about 0.5 to about 40; and,
    recovering epsilon-caprolactam.

12. The process described in claim 11 including the steps of recovering and recycling unconverted cyclohexane oxime.

13. The process described in claim 11 wherein said conversion conditions include a temperature of about 200° to about 400° C.

14. The process described in claim 11 wherein said crystalline zeolite has the crystal structure of ZSM-5.

15. The process described in claim 12 wherein said crystalline zeolite has the crystal structure of; ZSM-5.

16. The process described in claim 13 wherein said crystalline zeolite has the crystal structure of ZSM-5.

* * * * *